(12) United States Patent
Gussen et al.

(10) Patent No.: US 10,065,013 B2
(45) Date of Patent: Sep. 4, 2018

(54) SELECTIVE AMPLIFICATION OF AN ACOUSTIC SIGNAL

(71) Applicant: Ford Global Technologies, LLC, Dearborn, MI (US)

(72) Inventors: Uwe Gussen, Huertgenwald (DE); Frederic Stefan, Aachen (DE); Christoph Arndt, Moerlen Rheinland-Pfalz (DE)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 15/617,491

(22) Filed: Jun. 8, 2017

(65) Prior Publication Data
US 2017/0354796 A1     Dec. 14, 2017

(30) Foreign Application Priority Data

Jun. 8, 2016 (IN) .............................. 201641019749

(51) Int. Cl.
| | |
|---|---|
| H04R 29/00 | (2006.01) |
| A61M 21/02 | (2006.01) |
| G10K 11/178 | (2006.01) |
| G10L 15/08 | (2006.01) |
| G10L 21/0272 | (2013.01) |
| G10L 25/51 | (2013.01) |

(Continued)

(52) U.S. Cl.
CPC ........... *A61M 21/02* (2013.01); *G10K 11/178* (2013.01); *G10L 15/08* (2013.01); *G10L 21/0272* (2013.01); *G10L 25/51* (2013.01); *H04R 27/00* (2013.01); *A61M 2021/0027* (2013.01); *A61M 2205/3375* (2013.01); *A61M 2205/50* (2013.01); *G10K 2210/3044* (2013.01); *G10L 2015/088* (2013.01); *G10L 2021/02087* (2013.01); *H04R 2227/003* (2013.01); *H04R 2499/13* (2013.01); *H04S 7/30* (2013.01); *H04S 2400/15* (2013.01)

(58) Field of Classification Search
CPC ....................................................... H04R 29/00
See application file for complete search history.

(56) References Cited

U.S. PATENT DOCUMENTS

| | | | |
|---|---|---|---|
| 5,621,182 A | 4/1997 | Matsumoto | |
| 5,811,708 A | 9/1998 | Matsumoto | |

(Continued)

FOREIGN PATENT DOCUMENTS

JP         0911810 A     1/1997

*Primary Examiner* — Olisa Anwah
(74) *Attorney, Agent, or Firm* — Frank A. MacKenzie; Brooks Kushman P.C.

(57) ABSTRACT

The present subject matter relates to systems and methods for selectively amplifying an acoustic signal in a closed environment. In an implementation, a plurality of acoustic signals may be received from within the closed environment. Frequency ranges corresponding to each acoustic signal may be obtained and compared to determine presence of at least one individual in the closed environment. Acoustic signals pertaining to the at least one individual may be analysed to detect occurrence of a physiological event. Based on the analysis, the acoustic signal may be recognized as a target signal, and the target signal may be amplified in the closed environment. Further, an interfering signal may be generated to cancel other acoustic signals within the closed environment.

15 Claims, 3 Drawing Sheets

(51) Int. Cl.
*H04R 27/00* (2006.01)
*A61M 21/00* (2006.01)
*G10L 21/0208* (2013.01)
*H04S 7/00* (2006.01)

(56) References Cited

U.S. PATENT DOCUMENTS

| | | | |
|---|---|---|---|
| 5,817,965 | A | 10/1998 | Matsumoto |
| 5,857,171 | A | 1/1999 | Kageyama et al. |
| 5,876,213 | A | 3/1999 | Matsumoto |
| 6,151,571 | A | 11/2000 | Pertrushin |
| 6,326,536 | B1 | 12/2001 | Wang |
| 6,535,609 | B1 | 3/2003 | Finn et al. |
| 6,748,086 | B1 | 6/2004 | Venkatesh et al. |
| 9,955,937 | B2 * | 5/2018 | Telfort .................... A61B 7/04 |
| 2007/0255545 | A1 * | 11/2007 | Pita ....................... G01V 11/00 703/10 |
| 2011/0138127 | A1 * | 6/2011 | Ben-Yehuda ........... G06F 12/08 711/128 |
| 2013/0289424 | A1 * | 10/2013 | Brockway ............ A61B 5/0402 600/509 |
| 2015/0106095 | A1 * | 4/2015 | Mitchell ................ G10L 25/51 704/236 |
| 2016/0000365 | A1 * | 1/2016 | Kushki .................. A61B 5/165 600/481 |
| 2016/0150338 | A1 * | 5/2016 | Kim ........................ G08B 1/08 381/58 |
| 2016/0173049 | A1 * | 6/2016 | Mehta ..................... H03G 3/32 381/57 |
| 2016/0364963 | A1 * | 12/2016 | Matsuoka ................ H04R 3/00 |
| 2017/0291541 | A1 * | 10/2017 | Di Censo ............... B60Q 5/006 |

* cited by examiner

SELECTIVE AMPLIFICATION OF AN ACOUSTIC SIGNAL

CROSS REFERENCE TO RELATED APPLICATIONS

This application claims foreign priority benefits under 35 U.S.C. § 119(a)-(d) to IN Application 2016 41 019 749 filed Jun. 8, 2016, which is hereby incorporated by reference in its entirety.

TECHNICAL FIELD

The present subject matter relates, in general to amplification systems, and, in particular, selective amplification of an acoustic signal in a closed environment.

BACKGROUND

An amplification system is typically used to amplify acoustic signals, such as voices, for being heard by people in a nearby surrounding. In case of a closed environment, such as in a conference hall, the amplification system may be used to amplify the acoustic signals received from a particular person, such as a speaker, for enabling people at far end of the conference hall to hear the speaker. Generally, in the conference hall, the speaker is provided with a microphone to capture the voice of the speaker. The voice captured by the microphone is amplified and broadcasted through one or more loudspeakers that may be placed at different locations in the conference hall.

At times, there may be cases where there may be more than one speaker, such as in case where individuals are talking amongst themselves. In such cases, the microphones may capture more than one acoustic signal pertaining to more than one individual. In such a scenario, the amplification system has to be configured so as to amplify a particular acoustic signal. In absence of such configuration, the amplification system may amplify all the acoustic signals, and it may result in chaos.

The above situation may be explained with respect to an example. In case of a closed environment having a plurality of individuals, there may be instances where an individual is feeling uncomfortable, such as due to dizziness or other certain health conditions. In such cases, with so many voices being generated in the closed environment, it becomes difficult to hear the voice of the individual in discomfort. For example, if a child is separated from his parents and crying in the conference hall, the child's voice may get unnoticed between the voices of different individuals. As mentioned earlier, even though the microphones employed in the closed environment are able to capture the voices of the individuals in the closed environment, the existing techniques are unable to detect only the voice of the individual in discomfort.

Various approaches are known and disclosed in the state of the art to amplify the voices of individuals. One such approach is disclosed, for instance, in U.S. Pat. No. 6,535,609. U.S. Pat. No. 6,535,609 discloses a communication system for the interior cabin of a vehicle. The communication system includes a first microphone and a second microphone, positioned at a first location and a second location respectively within the cabin, for receiving spoken voices and converting the spoken voices into a first audible signal and a second audible signal respectively.

The communication system may further include a filtering device for providing first and second filtered audio signals responsive to the first and the second audio signals. Further, the communication system comprises a summer for summing the first and second compensated audio signals to provide a resultant audio signal indicative of a detection location within the cabin, relative to the first and second locations of the first and the second microphones. The communication system also includes an echo cancellation device for receiving the resultant audio signal and for outputting an echo-canceled audio signal. In addition, the communication system includes a loudspeaker for converting the echo-canceled audio signal into an output reproduced voice within the cabin.

SUMMARY

The subject matter described herein, relates to amplification of an acoustic signal. In one implementation, an audio engine may receive, in real-time, a plurality of acoustic signals from within a closed environment. The audio engine receives the plurality of acoustic signals from at least one sensor that may be employed at different locations within the closed environment. The audio engine may process the plurality of acoustic signals to obtain the frequency ranges for each of the plurality of acoustic signals. The audio engine may compare frequency ranges pertaining to each of the plurality of acoustic signals with frequency ranges of human voices to determine presence of at least one individual in the closed environment.

Further, an amplification engine may analyze acoustic signals pertaining to the at least one individual to detect occurrence of a physiological event in the closed environment. The physiological event may indicate a condition of discomfort to an individual. In an example, the physiological event may include one of an utterance of a pre-defined keyword and an occurrence of a pre-defined frequency range in the acoustic signal corresponding to the at least one individual. Based on the analysis, the amplification engine may select an acoustic signal as a target signal, wherein the target signal is indicative of the acoustic signal triggering the physiological event. Thereafter, the amplification engine may amplify the target signal within the closed environment and generate an interfering signal to cancel other acoustic signals within the closed environment.

In another implementation, acoustic signals pertaining to at least one individual may be analyzed to detect occurrence of a physiological event in the closed environment. Further, based on the analysis, an acoustic signal may be recognized as a target signal. The target signal is indicative of the acoustic signal triggering the physiological event. Based on the recognizing, the target signal is amplified within the closed environment. Furthermore, other acoustic signals in the closed environment may be cancelled.

Different features, aspects, and advantages of the present subject matter will be better understood with reference to the following description and the appended claims. The summary is provided to introduce a selection of concepts in a simplified form and is not intended to identify key features or essential features of the claimed subject matter, nor is it intended to be used to limit the scope of the claimed subject matter.

BRIEF DESCRIPTION OF THE DRAWINGS

The detailed description is provided with reference to the accompanying figures. It should be noted that the descrip

DETAILED DESCRIPTION

Figure 1:
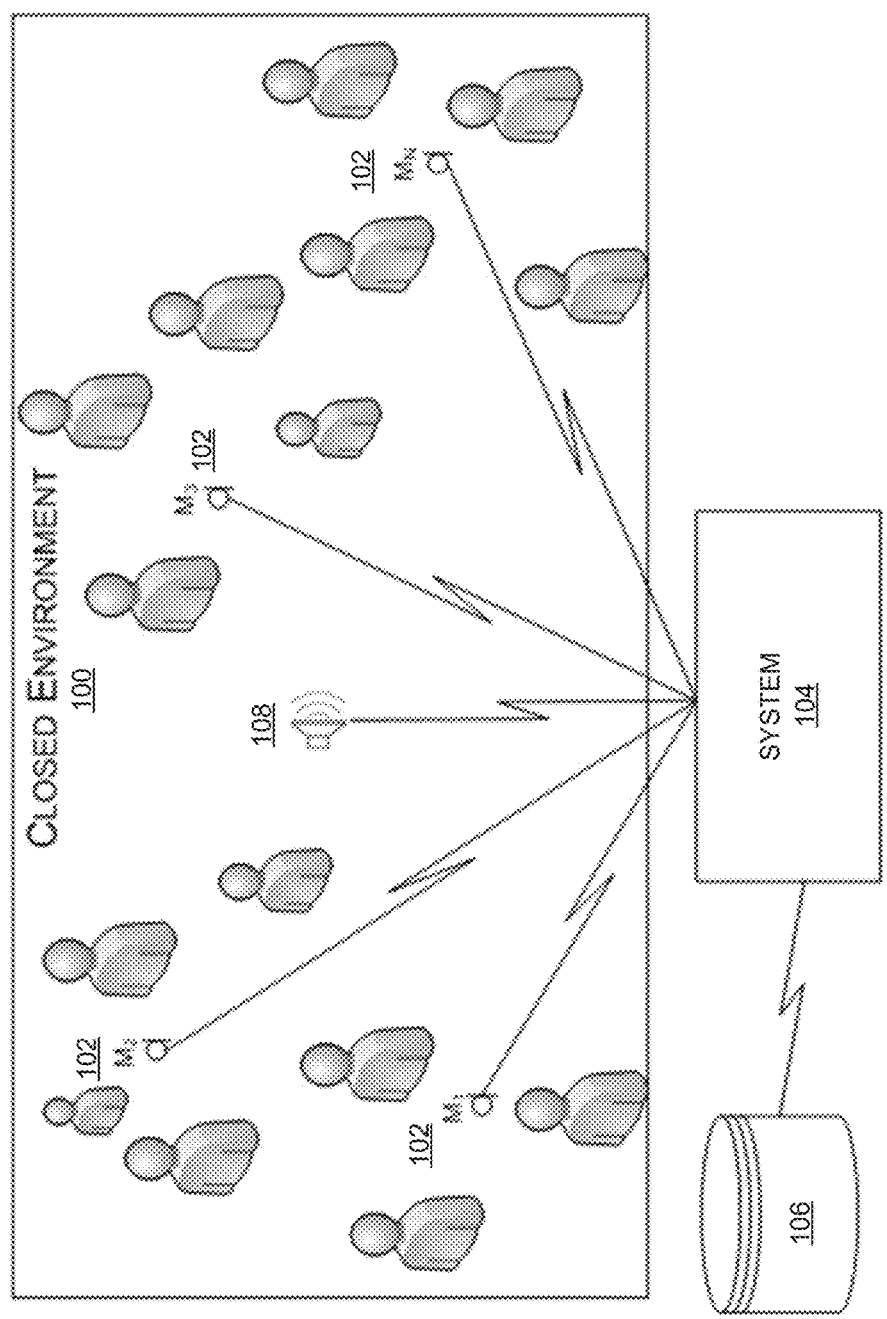
- FIG. 1 illustrates a network diagram depicting a closed environment employing an example system for selectively amplifying an acoustic signal, according to an implementation of the present subject matter.

As required, detailed embodiments of the present disclosure are disclosed herein; however, it is to be understood that the disclosed embodiments are merely exemplary of the disclosure that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure.

In cases of closed environment, when there are more than one sources of voice, there may be instances when voice of an individual may not be heard clearly by others. In an example, while travelling in a vehicle, the voice of the passengers may not be clear due to the ambient noise within a cabin of the vehicle as well as the voices of other passengers. As a result of this, the passengers may have to speak loudly for being able to be heard. In such situations, if the passenger, such as a child, is not feeling well or is crying within the vehicle, his voice may get subdued by the voices of other individuals in the vehicle, and a timely attention may not be provided to the person.

Further, due to the distance between passengers, communication amongst them may cause certain problems. Existing systems try to provide clarity of voice within an enclosed space, such as within a vehicle. For example, the existing systems provide microphones that may be used within a cabin of the vehicle to capture the voices of passengers. Thereafter, the voices may be processed to remove any ambient noise and to cancel any echo effect. The processed voices may then be amplified through in-built speakers of the vehicle. The existing systems thereby attempt to provide clarity of acoustic signals within the cabin.

However, amplification of the voice may not be sufficient in those cases where immediate attention is required, such as the case of a child as described above. In case of more than one source of voice, the existing systems may not be able to determine which voice to amplify. Removal of the ambient noise may not be sufficient in all situations.

To this end, approaches for selective amplification of an acoustic signal are described. Systems and methods employing these approaches may be implemented in a closed environment. The closed environment may be understood as a closed space, such as a conference hall, a theatre, and a cabin of a vehicle. In an implementation, the system may receive multiple acoustic signals from one or more sensors that may be employed within the closed environment. According to an aspect of the present subject matter, the multiple acoustic signals may be received in real time. The system may process the acoustic signals to obtain frequency ranges corresponding to each of the multiple acoustic signals. Further, the system may compare frequency ranges obtained for each of the multiple acoustic signals with frequency ranges of human voices to determine presence of individuals in the closed environment.

In an implementation, based on the comparison, the system may segregate the multiple acoustic signals. In an example, the system may segregate the multiple acoustic signals as acoustic signals received from individuals and other acoustic signals.

The system may thereafter, analyze the acoustic signals received from individuals to detect occurrence of a physiological event in the closed environment. The physiological event may be understood as an event associated with a physiological condition. Examples of the physiological event may include an utterance of a pre-defined keyword and an occurrence of a pre-defined frequency range, in the acoustic signals received from individuals. Upon detection of the physiological event, the system may select one acoustic signal from the acoustic signals received from individuals as a target signal. In an example, the acoustic signal triggering the physiological event may be selected as the target signal.

Based on the selection, the system may amplify the target signal within the closed environment. For example, the system may amplify the target signal through at least one audio output device that may be employed within the closed environment. In order to provide clarity to the amplified target signal, the system may generate an interfering signal to cancel the other acoustic signals within the closed environment. Thereby, the system cancels any unwanted sound while amplifying the target signal. The cancellation of the other acoustic signals may facilitate in clear amplification of the target signal.

In an example, the system may employ an active noise cancelation technique to cancel the other acoustic signals. Accordingly, the interfering signal so generated may have same frequency as the other acoustic signals in the closed environment. Further, the interfering signal is 180 degrees out of phase with the other acoustic signals. The system may, thereafter, add the interfering signal in the closed environment to cancel the other acoustic signals in the closed environment.

In operation, the present subject matter analyzes the acoustic signals received from individuals, to detect presence of a pre-defined keyword or a pre-defined frequency range in the acoustic signals received from individuals. As may be understood, the pre-defined keyword or the pre-defined frequency range may relate to the physiological condition, such as crying, shouting, and seeking help. Based on the analysis, the system selects an acoustic signal as a target signal. The target signal is indicative of the acoustic signal triggering the physiological event. The system may amplify the target signal in the closed environment, so that immediate attention may be paid to the individual in discomfort. In addition, the system cancels the other acoustic signals within the closed environment so that the amplified target signal may be clearly heard by others. The cancellation ensures that there is no disturbance in the amplified target signal.

The above mentioned implementations are further described herein with reference to the accompanying figures. It should be noted that the description and figures relate to exemplary implementations, and should not be construed as a limitation to the present subject matter. It is also to be understood that various arrangements may be devised that, although not explicitly described or shown herein, embody the principles of the present subject matter. Moreover, all statements herein reciting principles, aspects, and embodiments of the present subject matter, as well as specific examples, are intended to encompass equivalents thereof.

Figure 2:
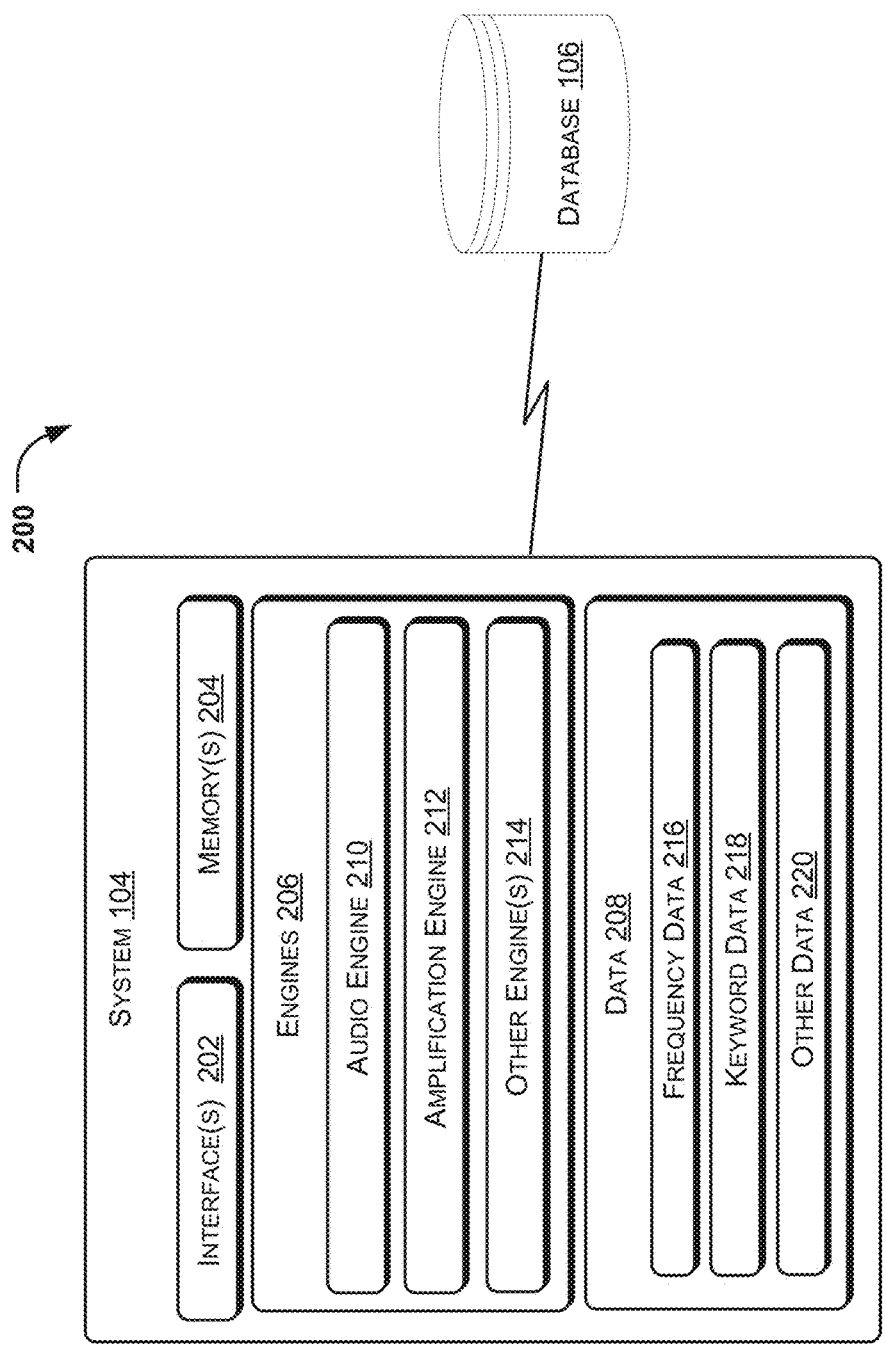
FIG. 2 illustrates a block diagram of an example system for selectively amplifying an acoustic signal in a closed environment, according to an implementation of the present subject matter.
Figure 3:
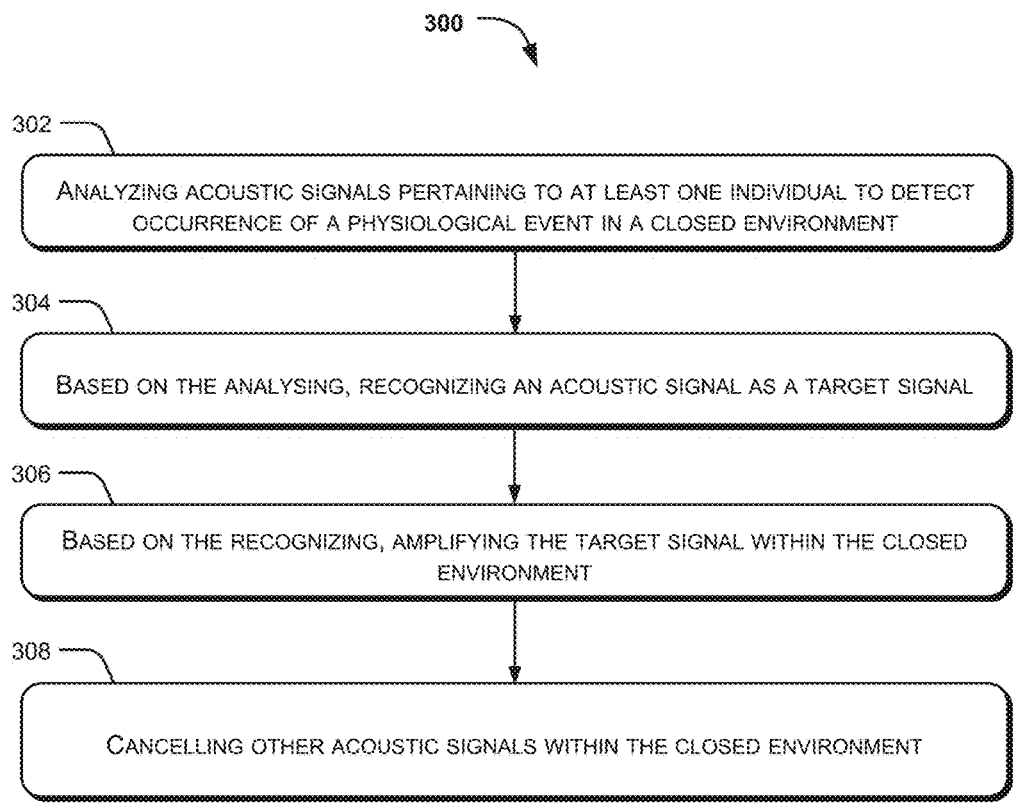
FIG. 3 illustrates a flowchart of an example method for selectively amplifying an acoustic signal in a closed environment, according to an implementation of the present subject matter.

These and other aspects are described in conjunction with one or more computing devices and their operations, as exemplified in FIG. 1-3. FIG. 1 illustrates a network diagram depicting a closed environment 100 employing an example system 104 for selectively amplifying an acoustic signal in the closed environment 100, according to an embodiment of the present subject matter. In an example, the closed environment 100 may be understood as an enclosed area. Examples of the closed environment 100 may include, but are not limited to, a conference hall, a theater, and a cabin of a vehicle. The closed environment may include one or more sources of sound. For example, if the closed environment is a cabin of a vehicle, the one or more sources of sound may include at least one passenger in the vehicle, entertainment system, engine, air-conditioner, and the like.

In the present embodiment, the closed environment 100 may include one or more sensors 102, hereinafter referred to as sensors 102, for capturing acoustic signals that may be generated within the closed environment 100. In an example, the sensors 102 may include microphones. In another example, the sensors 102 may include Micro-Electro-Mechanical Systems (MEMS). The sensors 102 may capture different acoustic signals from within the closed environment 100 in real-time. In an implementation, the sensors 102 may be coupled with a system 104. The system 104 may be configured to identify a target signal pertaining to an individual upon occurrence of a physiological event, within the closed environment 100.

In an implementation, the system 104 may receive the different acoustic signals captured by the sensors 102. The system 104 may, upon receiving the acoustic signals, process the different acoustic signals to determine acoustic signals received from individuals in the closed environment 100. For example, the system 104 may compare the frequency range of the different acoustic signals with frequency ranges of human voices to determine those acoustic signals that pertain to individuals. Further, the acoustic signals received from individuals may be analyzed to detect occurrence of the physiological event in the closed environment 100. The physiological event may be understood as an event associated with a physiological condition of an individual. For example, the physiological event may include utterance of a keyword by an individual or occurrence of a frequency range in the acoustic signals associated with the at least one individual.

In an implementation, the system 104 may be coupled with a database 106. The database 106 may store keywords as well as a plurality of frequency ranges that depict occurrence of the physiological event. For example, the frequency ranges corresponding to different physiological conditions, such as crying, anger, and pain.

Upon detection of the physiological event, the system 104 may select the acoustic signal triggering the physiological event as a target signal. Further, the system 104 may amplify the target signal within the closed environment 100. In an aspect of the present subject matter, the system 104 may be coupled with at least one loudspeaker 108, employed within the closed environment 100. The at least one loudspeaker 108 may facilitate in amplifying the target signal within the closed environment 100.

In addition, the system 104 may cancel other acoustic signals within the closed environment 100 such that the amplified target signal is audible to other individuals. In an implementation, the system 104 may employ active noise cancellation techniques to cancel the other acoustic signals within the closed environment 100. For example, the system 104 may generate an interfering signal to cancel the other acoustic signals within the closed environment 100. Accordingly, necessary attention or help may be provided to an individual in the closed environment 100.

These and other functionalities are provided in further detail in conjunction with FIG. 2. FIG. 2 illustrates a block diagram of the system 104, hereinafter referred to as the system 104, for selectively amplifying an acoustic signal in a closed environment 100, according to an implementation of the present subject matter. In an aspect of the present subject matter, the system 104 may be implemented in a hardware unit in the closed environment 100. In an example, when the closed environment 100 is a cabin of a vehicle, the system 104 may be implemented in an entertainment system of the vehicle. In another example, when the closed environment 100 is a conference hall, the system 104 may be implemented in a sound system of the conference hall.

In an implementation, the system 104 may be connected to the database 106. Although not shown in the figure, the database 106 may be connected to the system 104 over a network. In an example, the database 106 contains frequency pattern pertaining to human voices. Further, the database 106 may contain the pre-defined frequency patterns as well as pre-defined keywords for identification of the physiological event. Accordingly, the system 104 may utilize the database 106 to identify the acoustic signals pertaining to the individuals. Furthermore, the system 104 may utilize the database 106 to identify the target signal. For example, the database 106 may be used for storing acoustic signals, from the sensors 102, for being analyzed by the system 104; frequency ranges associated with the acoustic signals; and keywords associated with the acoustic signals.

Further, the system 104 includes interface(s) 202 and memory 204. The interface(s) 202 may include a variety of interfaces, for example, interfaces for data input and output devices, referred to as I/O devices, storage devices, network devices, and the like. The interface(s) 202 facilitates communication between the system 104 and various devices connected in the closed environment 100.

The memory 204 may store one or more computer-readable instructions, which may be fetched and executed, result in enabling the system 104 in amplifying a target signal. The memory 204 may include any non-transitory computer-readable medium, including, for example, volatile memory such as RAM, or non-volatile memory such as EPROM, flash memory, and the like. The system 104 further includes engine(s) 206 and data 208.

The engine(s) 206 is implemented as a combination of hardware and programming (for example, programmable instructions) to implement one or more functionalities of the engine(s) 206. In examples described herein, such combinations of hardware and programming may be implemented in a number of different ways. For example, the programming for the engine(s) 206 may be processor executable instructions stored on a non-transitory machine-readable storage medium and the hardware for the engine(s) 206 may include a processing resource (for example, one or more processors) to execute such instructions. In the present examples, the machine-readable storage medium stores instructions that, when executed by the processing resource, implement engine(s) 206. In such examples, the system 104 may include the machine-readable storage medium storing the instructions and the processing resource to execute the instructions, or the machine-readable storage medium may be separate but accessible to system 104 and the processing resource. In other examples, engine(s) 206 may be implemented by electronic circuitry.

The data 208 includes data that is either used or generated as a result of the functionalities implemented by any of the engine(s) 206. In an example, the engine(s) 206 includes the audio engine(s) 210, amplification engine 212, and other engine(s) 214. The other engine(s) 214 may implement functionalities that supplement applications or functions performed by the system 104. Further, the data 208 includes frequency data 216, keyword data 218, and other data 220.

In operation, the audio engine 210 may receive different acoustic signals from within the closed environment 100. The acoustic signals may originate from different sources, for example voice of a person, music from an entertainment source, and the like. In an implementation, the different acoustic signals may be received in real-time by the audio engine 210. In an aspect of the present implementation, the different acoustic signals may be received by the sensors 102 that may be employed within the closed environment 100. Examples of the sensors 102 may include, but are not limited to microphones and Micro-Electro-Mechanical sensors, that may be configured to feed real-time acoustic signals to the audio engine 210. In an example, the sensors 102 may be employed at different locations in the closed environment 100 to capture the acoustic signals. In another example, the sensors 102 may be pre-fitted in the closed environment 100, such as a cabin of a vehicle.

Further, the audio engine 210 may process the different acoustic signals to obtain the frequency ranges corresponding to each of the acoustic signals. In an example, the audio engine 210 may employ Kalman filtering technique to process the different acoustic signals in real time. As a result, the audio engine 210 may extract frequency range corresponding to each acoustic signal. The frequency ranges deduced by the audio engine 210 may be stored in the database 106 as the frequency data 216 for future reference.

As mentioned above, the closed environment 100 may have more than one sources of the acoustic signals. For example, in case of the cabin of the vehicle, the multiple acoustic signals may be generated from different sources, such as an engine of the vehicle, an entertainment system, passenger voices, and ambient noise. The audio engine 210 may compare the frequency ranges obtained for each acoustic signal with frequency range of human voice to determine presence of individuals in the closed environment 100. For example, if the acoustic signals have a frequency range within 85 to 155 Hz, the audio engine 210 may determine presence of at least one male adult in the closed environment 100. Likewise, acoustic signals having a frequency range of 165 to 255 Hz indicate presence of an adult female in the closed environment 100. Moreover, the audio engine 210 may detect presence of a child in the closed environment 100 when the acoustic signals have a frequency range of 250 to 650 Hz. In an aspect, the human voice frequency range may be pre-stored in the database 106.

Once the presence of at least one individual is determined in the closed environment 100, the audio engine 210 may segregate the acoustic signals pertaining to the at least one individual from other acoustic signals from amongst the different acoustic signals in the closed environment 100. The segregated acoustic signals pertaining to the at least one individual may be further processed by the system 104 to select an acoustic signal for being amplified, based on certain parameters. Accordingly, the audio engine 210 may eliminate or filter out unwanted acoustic signals. Therefore, a set of the acoustic signals is processed further, thereby facilitating in faster processing of the acoustic signals.

In another implementation, the system 104 may receive the acoustic signals pertaining to individuals for determination of the physiological event and identification of the target signal. For example, the multiple acoustic signals may be processed by a communication system of a conference hall and the communication system may be coupled with the system 104. The communication system may provide the acoustic signals pertaining to individuals to the system 104 for further analysis.

In an example, the amplification engine 212 may analyze the acoustic signals pertaining to the at least one individual to detect occurrence of a physiological event in the closed environment 100. In an example, the physiological event may be understood as an event associated with a physiological condition of the at least one individual. In the present example, the physiological condition may be understood as a condition of discomfort that may be experienced by an individual in the closed environment 100. Examples of the physiological conditions may include, but are not limited to, feeling nauseating, dizziness, pain, claustrophobia, or any condition of discomfort.

In an aspect of the present subject matter, the physiological event may include utterance of a pre-defined keyword or occurrence of a pre-defined frequency range in the acoustic signals corresponding to the at least one individual. For example, if a child is feeling nauseating within a vehicle, he may start crying. In such situations, the amplification engine 212 may compare a frequency range of child's cry with the pre-defined frequency ranges stored in the database 106. Based on the comparison, the amplification engine 212 may detect occurrence of the physiological event in the vehicle.

In another example, if a person is feeling dizzy in a crowded room, he may try to gain attention of others by calling out certain words, such as "help". In this case, the amplification engine 212 may detect utterance of the keyword "help" in the acoustic signal received from the individual. The amplification engine 212 may compare the keyword pronounced by the individual with pre-defined keywords stored in the database 106. The pre-defined keywords may be stored in the database 106 as the keyword data 218. When a match for the keyword or the frequency range is identified, the the physiological event is detected by the amplification module 212.

In an implementation, upon detection of the occurrence of the physiological event, the amplification engine 212 may select the acoustic signal triggering the physiological event as a target signal. Thereafter, the amplification engine 212 may amplify the target signal within the closed environment 100. In an example, the amplification engine 212 may amplify the target signal through at least one audio output device, such as a loudspeaker 108 that may be employed within the closed environment 100.

Further, the amplification engine 212 may cancel the other acoustic signals received from the closed environment 100, using active noise cancellation technique. In an aspect of the present subject matter, the amplification engine 212 may generate an interfering signal to cancel the other acoustic signals amongst the plurality of acoustic signals within the closed environment 100. In an example, the interfering signal may have same frequency as the other acoustic signals in the closed environment 100. In addition, the interfering signal is 180 degrees out of phase with the other acoustic signals. The amplification engine 212 may add the interfering signal to the closed environment 100 to cancel the other acoustic signals. It may be understood that the amplification engine 212 may employ any other noise cancelation techniques that may be existing in the art. Examples of existing noise cancelation techniques may include Multiple Signal Classification (MUSIC) method, the Pisarenko Harmonic Decomposition method, and the like.

The amplification of the target signal, i.e., the acoustic signal pertaining to the physiological event, within a certain range may facilitate in detecting any condition of discomfort in the closed environment. Further, the cancellation of the other acoustic signals within the closed environment enables recognition of the individual in discomfort.

FIG. 3 illustrates example method 300 to selectively amplify an acoustic signal, according to an implementation of the present subject matter. The order in which the method is described is not intended to be construed as a limitation, and any number of the described method blocks may be combined in any order to implement the aforementioned method, or an alternative method. Furthermore, method 300 may be implemented by processing resource or computing device(s) through any suitable hardware, non-transitory machine readable instructions, or combination thereof It may also be understood that method 300 may be performed by programmed computing devices, such as system 104 as depicted in FIGS. 1-2. Furthermore, the method 300 may be executed based on instructions stored in a non-transitory computer readable medium, as will be readily understood. The non-transitory computer readable medium may include, for example, digital memories, magnetic storage media, such as one or more magnetic disks and magnetic tapes, hard drives, or optically readable digital data storage media. The method 300 is described below with reference to system 104 as described above; other suitable systems for the execution of these methods may also be utilized. Additionally, implementation of these methods is not limited to such examples.

Referring to FIG. 3, at block 302, the method 300 may include processing a plurality of acoustic signals received from the closed environment 100. In an implementation, an audio engine 210 may process the plurality of acoustic signals to obtain a frequency range for each of the plurality of acoustic signals. In an example, the plurality of acoustic signals is received in real time by the audio engine 210.

At block 304, the method 300 may include comparing the obtained frequency ranges of each acoustic signal, to determine a presence of at least one individual in the closed environment 100. In an implementation, the audio engine 210 may be configured to compare the obtained frequency ranges with frequency ranges of human voices to determine the presence of the at least one individual.

At block 306, the method 300 may include analyzing the acoustic signals pertaining to the at least one individual to detect occurrence of a physiological event in the closed environment 100.

In an implementation, the amplification engine 212 may be configured to analyze the acoustic signals to detect occurrence of the physiological event. In an example, the physiological event may be understood as an event corresponding to a physiological condition of the at least one individual. In an aspect of the present subject matter, the physiological event may include one of an utterance of a pre-defined keyword and an occurrence of a pre-defined frequency range.

Further, at block 308, the method 300 may include selecting, based on the analyzing, an acoustic signal as a target signal. In an implementation, the amplification engine 212 may be configured to select the target signal. In an example, the target signal may be understood as the acoustic signal triggering the physiological event.

At block 310, the method 300 may include amplifying the target signal within the closed environment 100. In an implementation, the amplification engine 212 may be configured to amplify the target signal. In an example, the amplification may be made through an audio output device that may be employed within the closed environment 100.

Further, the amplification engine 212 may cancel the other acoustic signals amongst the plurality of acoustic signals. In this respect, the amplification engine 212 may generate an interfering signal to cancel the other acoustic signals.

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure. Additionally, the features of various implementing embodiments may be combined to form further embodiments of the disclosure.

What is claimed is:

1. A system comprising:
    an audio engine configured to compare frequency ranges obtained via a Kalman analysis for each of a plurality of acoustic signals having frequency ranges that determine a presence of an individual in a closed environment; and
    an amplification engine configured to, in response to a target signal indicative of a pre-defined keyword utterance, amplify the target signal within the closed environment and generate an interfering signal to cancel other acoustic signals.

2. The system as claimed in claim 1, wherein the plurality of acoustic signals is received from at least one sensor employed at different locations within the closed environment.

3. The system as claimed in claim 2, wherein the at least one sensor comprises at least one of a microphone and a plurality of Micro-Electro-Mechanical Sensors.

4. The system as claimed in claim 1, wherein the audio engine is further configured to segregate the acoustic signal received from the individual from the other acoustic signals in the closed environment.

5. The system as claimed in claim 1, wherein the physiological event is indicative of a condition of discomfort to an individual.

6. The system as claimed in claim 1, wherein the interfering signal has a frequency that is 180 degrees out of phase with the other acoustic signals.

7. The system as claimed in claim 1, wherein the amplification engine is coupled with a loudspeaker placed within the closed environment.

8. A method to amplify acoustic signals comprising;
    comparing, via an audio engine implementing a Kalman analysis, frequency ranges of acoustic signals pertaining to an individual;
    analyzing, by an amplification engine, the acoustic signals to detect a target signal indicative of a physiological event having a pre-defined frequency range in the closed environment;
    recognizing the target signal;
    amplifying the target signal within the closed environment; and
    cancelling other acoustic signals in the closed environment.

9. The method as claimed in claim 8, wherein the acoustic signals are received in real-time.

10. The method as claimed in claim 8, wherein the cancelling further includes
   generating, by the amplification engine, an interfering signal having same frequency as the other acoustic signals in the closed environment, wherein the interfering signal is 180 degrees out of phase with the other acoustic signals; and
   adding, by the amplification engine, the interfering signal to the closed environment to cancel the other acoustic signals in the closed environment.

11. A vehicle infotainment system, comprising:
   a processor configured to,
   receive, in real-time, a plurality of acoustic signals from within a closed environment;
   compare, using a Kalman analysis, frequency ranges of acoustic signals pertaining to an individual;
   analyze acoustic signals pertaining to at least one individual from the plurality of acoustic signals to detect occurrence of a physiological event being one of an utterance of a pre-defined keyword and an occurrence of a pre-defined frequency range in the acoustic signals in the closed environment;
   based on the analysis, select an acoustic signal corresponding to the at least one individual as a target signal, wherein the target signal is indicative of the acoustic signal triggering the physiological event;
   amplify the target signal within the closed environment, based on the identification; and
   generate an interfering signal to cancel other acoustic signals amongst the plurality of acoustic signals.

12. The infotainment system as claimed in claim 11 further comprising at least one sensor employed at different locations within the closed environment configured to measure the plurality of acoustic signals.

13. The infotainment system as claimed in claim 12, wherein the at least one sensor comprises at least one of a microphone and a plurality of Micro-Electro-Mechanical Sensors.

14. The infotainment system as claimed in claim 11, wherein the processor is further configured to segregate the acoustic signal received from the individual from the other acoustic signals in the closed environment.

15. The infotainment system as claimed in claim 11, wherein the physiological event is indicative of a condition of discomfort to the at least one individual.

\* \* \* \* \*